United States Patent [19]
Wolter et al.

[11] Patent Number: 5,132,115
[45] Date of Patent: Jul. 21, 1992

[54] PLANAR THERAPEUTIC SYSTEM, PROCESS FOR ITS PRODUCTION AND UTILIZATION

[76] Inventors: Karin Wolter, Altwieder Str. 46, D-5451 Melsbach; Fritz Herrmann, Rheinheldestr. 12c; Hans R. Hoffmann, Burghofstrasse 113, both of D-5450 Neuwied 12; Günter Simon, Tulpenweg 1, D-5533 Hillesheim; Thomas Kissel, Federerweg 10, D-7801 Ehrenkirchen 1; Joerg Reinhardt, Schauinslandstr. 5, D-7801 Ehrenkirchen, all of Fed. Rep. of Germany

[21] Appl. No.: 715,727
[22] PCT Filed: Apr. 16, 1987
[86] PCT No.: PCT/DE87/00174
§ 371 Date: Jan. 14, 1988
§ 102(e) Date: Jan. 14, 1988
[87] PCT Pub. No.: WO87/06144
PCT Pub. Date: Oct. 22, 1987

Related U.S. Application Data

[63] Continuation of Ser. No. 534,368, May 4, 1990, abandoned, which is a continuation of Ser. No. 306,278, Feb. 2, 1989, abandoned, which is a continuation of Ser. No. 139,255, Jan. 14, 1988, abandoned.

[30] Foreign Application Priority Data

Apr. 17, 1986 [DE] Fed. Rep. of Germany ....... 3613002
Oct. 6, 1986 [DE] Fed. Rep. of Germany ....... 3634016

[51] Int. Cl.⁵ .................................. A61F 13/02
[52] U.S. Cl. ......................... 424/448; 424/449
[58] Field of Search .......................... 424/448, 449

[56] References Cited

U.S. PATENT DOCUMENTS

| | | | |
|---|---|---|---|
| 4,687,481 | 8/1987 | Nuwayser | 424/449 |
| 4,699,792 | 10/1987 | Nick | 424/449 |
| 4,711,781 | 12/1987 | Nick | 424/449 |

FOREIGN PATENT DOCUMENTS

| | | |
|---|---|---|
| 147119 | 3/1985 | European Pat. Off. |
| 3202775 | 3/1983 | Fed. Rep. of Germany |
| 106616 | 7/1982 | Japan |

*Primary Examiner*—Thurman K. Page
*Assistant Examiner*—D. Gabrielle Phelan
*Attorney, Agent, or Firm*—Kalish & Gilster

[57] ABSTRACT

A transdermal therapeutic system is disclosed which comprises an optional flexible backing layer, one or more drug reservoir(s), one or more adhesive layer(s) and optionally a detachable protective layer for the skin contact surface of the flat therapeutical system. The skin contact area of the therapeutical system is a skin contact layer which has one or more non-adhesive drug-releasing section(s) and one or more skin-adhesion section(s), which optionally contain a further drug. A process is disclosed for the production of the system, as well as the use thereof for local or systemic, transdermal administration of drugs in human or veterinary medicine or in cosmetics.

37 Claims, 4 Drawing Sheets

PLANAR THERAPEUTIC SYSTEM, PROCESS FOR ITS PRODUCTION AND UTILIZATION

This application is a continuation of Ser. No. 07/534,368, filed May 4, 1990, now abandoned, which is a continuation of Ser. No. 07/306,278, filed Feb. 2, 1989, now abandoned, which is a continuation of Ser. No. 1 07/139,255, filed Jan. 14, 1988, now abandoned.

This invention relates to a transdermal therapeutic system for the administration of drugs to the skin, including drug reservoir(s) having drug-releasing areas and including skin adhesion regions arranged on the skin side thereof, and to a process for the production of the therapeutic system, and to its use.

The invention is thus concerned with a transdermal therapeutic system for the administration of medicinal substances and also cosmetically effective substances to human or animal skin.

The term "therapeutic system" includes a device comprising medicaments or active substance, and an administration form, which emits one or several active agents at a pre-determined rate continuously over a fixed period of time to a pre-determined area of application.

These systems are therapeutical precision instruments, the construction of which requires exceptional provisions to ensure continuous release of the active agent.

Therapeutic systems have already been developed for various applications and also for the skin, whereby systemic as well as topical activity can be attained. The variety of active agents applicable in this way, and their different chemical, physical and pharmacological properties make it impossible to solve all therapeutic problems with only one system.

A variety of flat therapeutic systems has already become known for the administration of medicinal substances to the skin. A summary thereof may be found e.g. in "Klaus Heilmann: Therapeutische Systeme, Ferdinand Enke Verlag, Stuttgart, 1977." However, a completely satisfactory effect may not be obtained in all cases by the state of the art systems.

A conventional construction of a known transdermal therapeutic system comprises a drug reservoir in which the active substance is present in solid, liquid or dissolved form, and a layer of pressure-sensitive adhesive by which the system can be brought into close contact with the skin.

This principle is limited in cases in which the active substance does not diffuse through the adhesive layer, or where a chemical reaction occurs between the active substance and the adhesive, or where the active substance is insoluble or only poorly soluble in the adhesive. In these cases, it has been attempted to bring a non-adhesive drug-containing reservoir or the drug itself into direct contact with the skin, and to fix this reservoir or the drug itself to the skin by additional means. For this purpose, separate adhesive, e.g., in the form of strips, is suitable, or the integration of the reservoir or the drug into a plaster can be employed, such that the reservoir or the drug is surrounded by an adhesive edge (see for example DE-OS 29 02 183). If the area of contact exceeds a certain size, the constant contact with the skin which is necessary for controlled therapy is not longer ensured after wearing this type of product for an extended time, such as days or even weeks, because of the unavoidable body and muscle movements.

In DE-OS 32 02 775, it has been proposed that the drug be distributed like a screen on the adhesive surface. In principle, the resulting adhesive surface is large enough for the drug to be fixed to the skin, and should in theory allow flat fixation of the drug reservoir. However, since the drug is not on the same level as the adhesive layer, this layer is constantly under stress after adhesion to the skin. For this reason, the joined areas can loosen again very easily with the inevitable body and muscle movements, and thus affect the constant contact of the surface of the drug with the skin due to changes in pressure which arise, and thereby prevent a controlled release of the drug.

A self-adhesive plaster having separate drug segments is known from DE-OS 34 23 328. In this product, cup-shaped drug segments and adhesive segments are arranged on a non-adhesive base. This arrangement is said to provide adhesive segments and drug segments on the same level. When applying the plaster, the size of the skin contact area and thus the amount of drug released depends on the pressure of the plaster paster. This plaster cannot be used as a therapeutic system.

In DE-OS 33 19 469, it has been proposed that a drug be deposited in the pores of a micro-porous film, which may be coated partially or entirely with an adhesive so as to fix the film to the skin. In this arrangement also, contact of the drug in the pore openings of the skin is affected, since the pore openings are not at the same level as the adhesive areas and consequently contact between the drug and the surface of the skin is prevented by the adhesive layer. Therefore, with this system also, controlled administration of drugs is not possible.

It is an object of the invention to provide a therapeutic system for administering drugs to the skin, which ensures constant contact of the drug-releasing area with the skin, independently of the required size of the drug-releasing area, even when the system is applied for a long period of time.

Thus, the problem is solved by a flat (planar) therapeutic system in which the drug-releasing section(s) to be brought into contact with the skin and the skin adhesion section(s) are at the same level (on the same plane) for being capable of simultaneous contact with the skin. The system according to the invention is especially advantageous for the administration of drugs which react unfavorably with the adhesive or which do not diffuse through an adhesive layer on the skin.

In a preferred embodiment of the invention, the drug-releasing sections are distributed regularly or irregularly over the skin contact area. It is particularly advantageous if the drug-releasing in shape sections are round (circular) or square in horizontal cross section. In the skin contact area, skin-adhesion sections may be distributed regularly or irregularly. The skin-adhesion sections are preferably round or square in horizontal cross section. For certain usages, however, it may be especially preferable for the skin-adhesion and drug-releasing sections to be arranged in strips alternating side-by-side. In an especially preferred embodiment of the invention, the skin contact area may have a peripheral skin-adhesion edge portion. The system according to the invention may also have a flexible backing layer facing away from the skin and, optionally, a detachable protective layer. In order to improve the mechanical stability, it may additionally possess a support layer with openings. The support layer may be paper, a textile sheet, a metal or plastic film or laminates thereof. An adhesive layer may be present wholly or partly between the support layer and the drug reservoir. The drug reservoir may comprise one or more active agent(s) with topical or systemic action.

The active agent (drug) is preferably selected from the group consisting of cardiac glycosides consisting of digitalis lanata-β-acetyl-digoxin; vasodilators, e.g., pentaerythrityl tetranitrate, cinnarizine or nitroglycerine, musculotropic spasmolytics, for example moxaverine HCl; coronary therapeutics, e.g. oxyfedrine HCl, coronary vasodilators, e.g. (N-(3,3-diphenylpropyl)-alpha-methyl-benzylamine HCl (fediline); anti-histamines such as clemastine or anti-emetic-dimethhydrinate, analeptics such as caffeine; analgesics such as penazone chloral hydrate; hypnotics such as chlorobutanol, musculotropic vasodilators, such as nicotinic acid, vitamin B6, such as pyridoxine, broncholytics, cardiacs, diuretics, phospho-diesterase inhibitors, theophylline and compounds thereof, for example oxytriphylline, aminophylline, theophylline sodium glycinate, theophylline sodium salicylate; as well as theophylline derivatives, bromotheophylline, chlorotheophylline, etamiphyllin, diprophylline, etophylline and proxyphylline, as well as rubefacients, such as nicotinic acid-β-butoxyethylester and/or nonyl acid vanillylamide; anti-phlogistics, such as ethyleneglycol monosalicylate or diethylamine salicylate. Preferred active agents include amphetaminil, betahistine, beta-acetyldigoxin, bopindolol, buprenorphine, clemastine, diclofenac, diltiazen, dimenhydrinate, diethylamine salicylate, ethyleneglycol monosalicylate, 5-fluorouracil, glibenclamide, hydromorphone, ibuprofen, isopropyl-4-(2,1,3-benzoxydiazol-4-yl)-1,4-dihydro-5-methoxycarbonyl-2,6-dimethyl-3-pyridine-carboxylate, ketotifen, L-thyroxine, nicotine, nicotinic acid-β-butoxyethylester, nonyl acid vanillylamide, pindolol, salbutamol, tamoxifen, tizanidine, as well as bases, salts and derivatives thereof. The active agents can also be used together in significant combinations. Preferred are A. Cardiac glycosides comprising digitalis lanata-β-acetyl-digoxin, in combination with
  1. a vasodilator, e.g. pentaerythrityl tetranitrate or nitroglycerine,
  2. a musculotropic spasmolytic, e.g. moxaverine HCl
  3. a coronary therapeutic, e.g. oxyfedrine HCl or
  4. a coronary vasodilator, e.g. N-(3,3-diphenylpropyl)-alpha-methyl-benzylamine HCl (fendiline)
B. Anti-histamine, clemastine, in combination with a gluco-cordicoid, e.g. dexamethasone or clorcortolone-21-pivalate;
C. Anti-histamine, such as anti-emetic-dimenhydrinate—in combination with a
  1. vasodilator, anti-histamine, e.g. cinnarizine,
  2. analeptic, e.g. caffeine,
  3. analgetic, antipyretic, e.g. phenazone chloralhydrate;
  4. hypnotic, anaesthetic, antiseptic, e.g. chlorobutanol;
  5. musculotropic vasodilator, lipid lowering agent, e.g. nicotinic acid, or
  6. vitamin B6, e.g. pyridoxine.
D. Broncholytic, cardiac, diuretic, phospho-diesterase inhibitor—theophylline—in combination with other
  1. theophylline compounds, such as:
    oxytriphylline,
    aminophylline,
    theophylline sodium glycinate
    theophylline sodium salicylate, or
  2. theophylline derivatives, such as:
    bromotheophylline
    chlorotheophylline
    stamiphyllin
    diprophylline
    etophylline
    proxyphylline
E. Rubefacient, such as nicotinic acid-β-butoxyethylester and/or nonyl acid vanillylamide—in combination with an anti-phlogistic, e.g. ethyleneglycol monosalicylate or diethylamine salicylate.

One particular advantage which can be achieved by such combinations of active agents is that ideally several active agents may be administered simultaneously, optionally with differing rates of release, whereas these agents cannot usually be processed or stored in a mixture, whether because they react together or because of differing physical properties. The stages of production illustrated further below allow the active ingredients to be worked in separately without problems.

Especially preferred active agents which may be used in the system according to the invention are: amphetaminil, betahistine, β-acetyldigoxin, bopindolol, buprenorphine, clemastine, diclofenac, diltiazen, dimenhydrinate, diethylamine, salicylate, ethyleneglycol monosalicylate, 5-fluorouracil, glibenclamide, hydromorphone, ibuprofen, isopropyl-4-(2,1,3-benzoxydiazol-4-yl)-1,4-dihydro-5-methoxy-carbonyl-2,6-dimethyl-3-pyridine-carboxylate, ketotifen, L-thyroxine, nicotine, β-butoxyethylester of nicotinic acid, vanillylamide of nonyl acid, pindolol, salbutamol, tamoxifen, tizanidine, theophylline, as well as the bases, salts and derivatives of the above-mentioned preferred agents.

The invention also relates to a process for the production of the therapeutic system, comprising the steps of providing an adhesive base material producing a skin adhesion layer on the base material; lining the base with a support material; perforating the laminate thus formed, replacing the adhesive base material by a detachable protective layer; coating the surface which is free from the protective layer with a drug reservoir material comprising a drug; lining the backing layer which optionally has an adhesive finish, and packaging the system.

In an especially preferred embodiment of this process, after perforating the laminate, a coating of the drug-containing reservoir material is made by lining with a drug-containing reservoir layer produced on the backing layer under pressure or under pressure/heat.

In a further especially preferred process embodiment, skin adhesion sections are applied to a protective base layer, these skin-adhesion layer sections and the protective base layer are coated with drug-containing reservoir material, the backing layer which optionally has an adhesive finish is lined, and the completed system is packaged.

The invention is further directed to the use of the system for the local or systemic transdermal adminstration of drugs in human or veterinary medicine or in cosmetics.

By arranging the therapeutically required drug-releasing areas alternately with adhesive areas on the same level (Plane) in accordance with the invention, a satisfactory, long-lasting, intimate contact of the drug-releasing reservoir with the skin surface which absorbs the drug is achieved so that a continuous uninterrupted supply of the drug is provided in accordance with therapeutical requirements.

Embodiments of the invention will now be described, by way of example, with reference to the accompanying drawings, in which.

In accordance with the invention, the skin contact layers may be classified according to two basic principles:

Principle A

The drug-releasing sections are individually distributed over a skin adhesion area which optionally also contains drugs.

Principle B

A drug-releasing area is broken up by a skin adhesion area which optionally also contains drugs.

Figure 1:
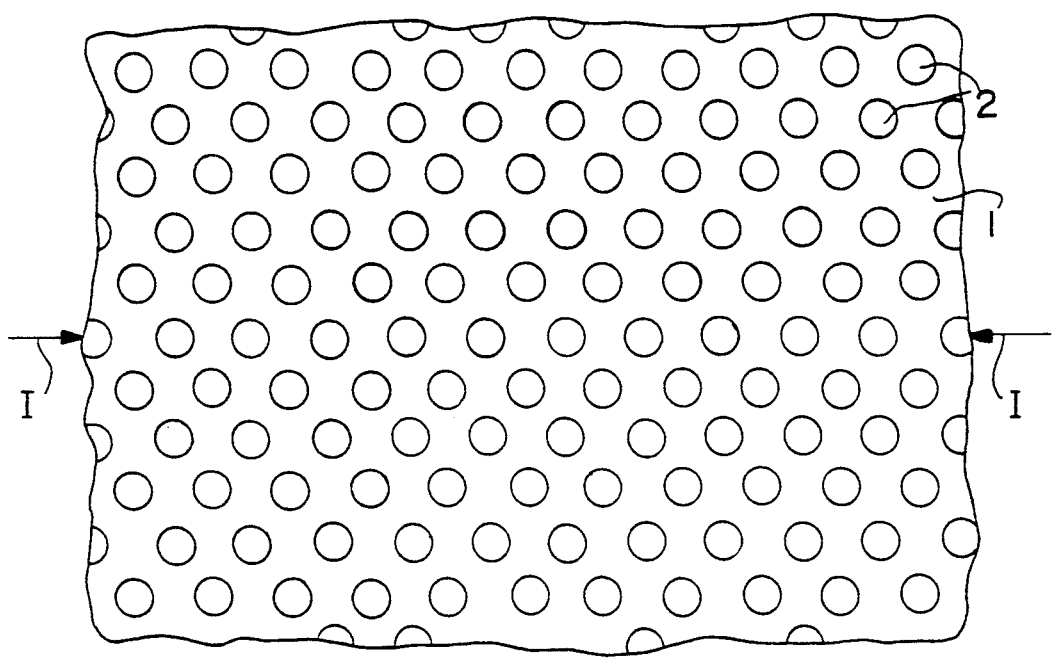
FIG. 1 shows a schematic view of the skin contact area of a section of a therapeutic system according to an embodiment of the invention.
Figure 2:
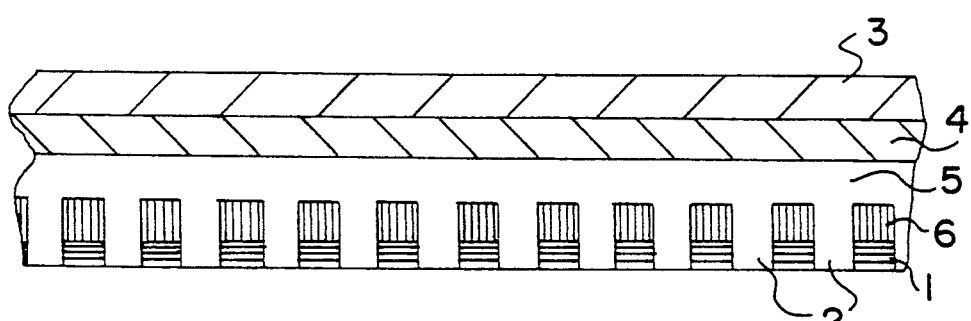
FIG. 2 is an enlarged cross-section along line I—I of FIG. 1.
Figure 3:
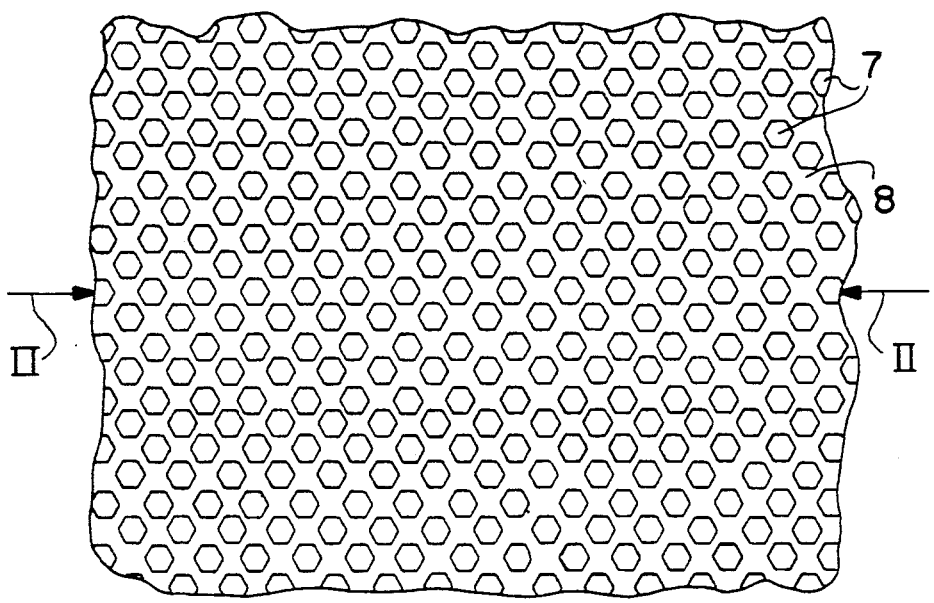
FIG. 3 shows a section of the skin contact area of a further preferred embodiment of the invention.
Figure 4:
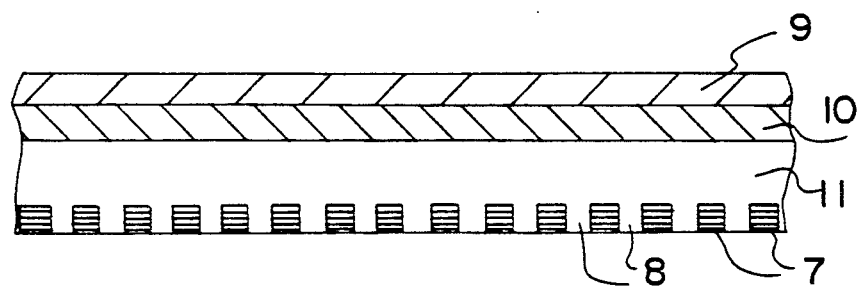
FIG. 4 is an enlarged cross-section along line II—II of FIG. 3.
Figure 5:
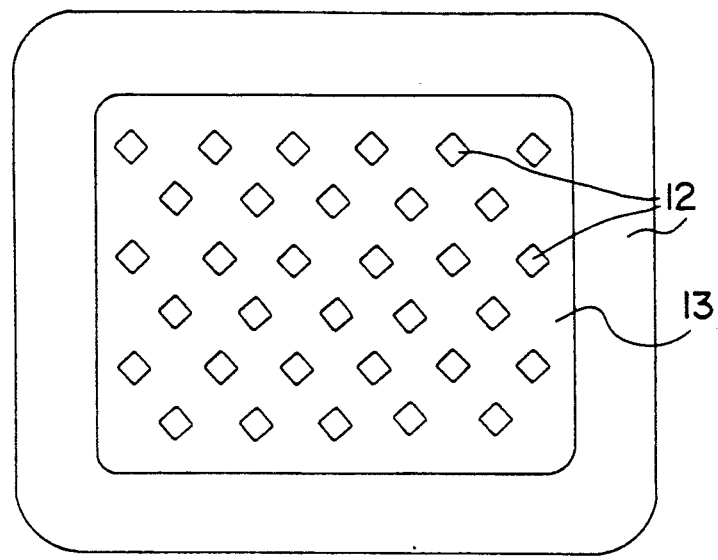
FIG. 5 shows the skin contact area of a plaster-like embodiment of the invention.
Figure 6:
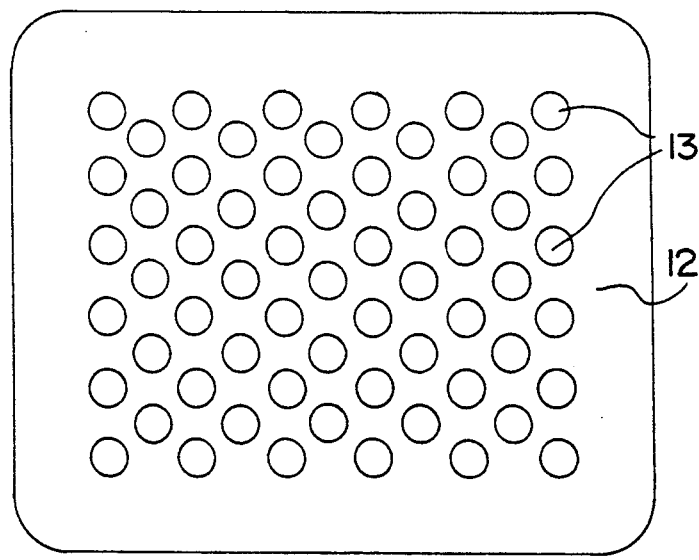
FIG. 6 shows the skin contact area of a further plaster-like embodiment of the invention.

Embodiments of the invention according to principle A are illustrated in FIGS. 1, 2 and 6; while FIGS. 3, 4 and 5 show embodiments corresponding to principle B.

In FIGS. 1 and 2, circular drug-releasing areas 2 are distributed symmetrically over an adhesive skin adhesion area 1. Of course, this embodiment should only be regarded as an example, and is not intended to limit the scope of the invention since the arrangement of the drug-releasing areas, their size, their geometric form and their distance from one another are variable and depend on the therapeutic and physical requirements.

Referring now to FIG. 2, an adhesive layer 4 which ensures cohesion with a drug reservoir layer 5 is arranged under a backing layer 3. The reservoir layer 5 is overlapped by a perforated support layer 6 which has a skin adhesion layer 1 on the skin side thereof. The hollow spaces resulting from perforation are completely filled by material from the drug reservoir 5, which in this case also forms the drug-releasing sections 2, so that drug-releasing sections 2 and skin adhesion sections 1 alternate on a single level of the skin contact surface (apparatus).

FIG. 6 shows a plaster-like embodiment according to principle A, whereby individual drug-releasing sections 13 are distributed symmetrically according to the invention as circular areas in the middle region of an otherwise adhesive plaster-like segment. Along the edge a peripheral, continuous adhesive area edge 12 is provided which, when applying the plaster, ensures secure joining of the edges with the skin.

FIGS. 3 and 4 illustrate a preferred embodiment according to principle B. In this embodiment, a drug-releasing area 8 is interrupted by symmetrically arranged hexagonal skin adhesion section 7. In this case also, the arrangement of the adhesive areas, their distances from one another, their size and their geometric forms are variable and may be changed as required. The structure of the system shown from the skin contact area in FIG. 3 may be appreciated from the greatly enlarged cross-section shown in FIG. 4. A backing layer 9 is provided to an intermediate layer 10, which in turn, contacts a reservoir layer 11. Disposed in the reservoir layer 11 are skin adhesion areas 7, which are on a single level with the surface of the drug reservoir 11 and are capable of forming a seal with the skin. The contact areas 7 are thus surrounded by the drug-releasing areas 8.

FIG. 5 illustrates a further embodiment in accordance with principle B, in the form of a plaster-like segment which is ready for application. The skin adhesion sections are marked 12 and the drug-releasing areas 13. In this form, the drug-releasing area is symmetrically interrupted by quadratic skin adhesion areas, and is surrounded by a peripheral skin adhesion edge portion. In this case also, it is especially advantageous that problems regarding the adhesion of the edges in the plaster-like systems of the invention can thus be avoided.

The new flat therapeutic systems according to the invention are capable of widely different applications, since—apart from special embodiments as are illustrated for example in FIGS. 5 and 6—they are produced as continuous lengths and can therefore be cut up into almost any size. They can be applied for example as plasters, strips or even bandages. By cutting up the lengths at random, it is possible that cut edges are produced which are not completely covered with adhesive. It is preferable, therefore, for care to be taken that the cutting lines always pass through such adhesive strips, rings etc.

By making an appropriate choice of geometric design of the system, the sections which are free from skin-adhesion material can be kept small, so that even when wearing the plaster for a long time, the edges do not become detached. The expanse of the tolerable sections which are free from skin-adhesion material depends on the choice of skin-adhesion material. A special case in this connection is a therapeutic system in which the drug-releasing area is distributed in strips over the skin adhesion area, or the skin adhesion area is distributed in strips over a drug-releasing area. Then, the cut need only be made parallel to the direction of the strips within an adhesive strip, so as to avoid having a completely non-adhesive edge.

The new system is especially suitable for transdermal administration of medical or cosmetic drugs, which cannot be applied from existing adhesive-containing systems or only with difficulty. However, all drugs which are simple to apply and which are able to migrate into the skin alone or with aids, can be used.

It has already been shown that the system is especially suitable for administering drugs, for example ketotifen orbopindolol.

The drug reservoir layer can be produced in a manner known per se. e.g. by dissolving the drug in a matrix material, dispersing the drug in a matrix or distributing the drug in a matrix in micro-encapsulated form; or dispersing the drug adsorbed on an inert carrier in a matrix. Of course, the drug reservoir may also consist of pure drug or essentially pure drug. The matrix itself may comprise low or high molecular, natural or synthetic material, while the choice thereof depends on the properties of the drug to be administered and the therapeutic requirements, as are familiar to experts in this field. In connection with ketotifen and bopindolol, for example, a matrix based on polyacrylates which may swell in water has proven especially good.

As well as the matrix components and drugs, the drug reservoir layer may comprise further suitable additives which will be known or obvious to the artisan, for example dissolving aids, softeners, stabilizers, fillers and enhancers. The thickness of the reservoir layer, i.e. the space between the support layer and the backing layer, which optionally has an adhesive finish, is mainly determined by the therapeutic demands on the system. It is preferable for the total thickness of the system to be between 40 $\mu$m and 5 mm, preferably between 80 $\mu$m and 1.2 mm. In special cases, the reservoir consists only of the complete or partial filling of the pore openings in the laminate which comprises the support layer and the skin adhesion layer, so that the backing layer, which has an adhesive finish, is in direct contact with the support layer. In this embodiment also, the drug-releasing surfaces are on the same level as the skin adhesion surfaces, as is required according to the invention.

The backing layer covering the reservoir on the side away from the skin may be permeable or impermeable. It must be flexible and is mainly used for providing further mechanical stability to the system. If parts of the reservoir or of the incorporated drugs are volatile the backing layer for these drugs must be impermeable. It may have one or several layers. Substances which can be used in its production include polymeric substances, for example polyethylene, polypropylene, polyethylene terephthalate and polyamides. Further possible materials include metal sheets, for example aluminium foil, alone or coated with a polymeric substrate. Permeable backing layers include, for example, textile sheets, such as woven and fleecy materials or even porous polymer materials. The required thickness of the backing layer depends on the material selected, but should be in the range from 5 to 150 micrometers, preferably between 10 and 60 micrometers. If the self-adhesiveness of the reservoir layer is not sufficient for a long-term union with the backing layer, adequate union may be attained using an adhesive intermediate layer, whereby the adhesive forces between the backing and intermediate layers must be greater than those between the skin contact surface and the skin. All physiologically acceptable adhesives which are inert towards drugs and the remaining components of the reservoir are suitable, e.g. those based on rubber, rubber-like synthetic homo-, co- or block-polymers, polyacrylic acid, esters and their copolymers, polyurethanes and silicones. The thickness of the adhesive intermediate layer 10 is preferably between 10 and 100 $\mu$m, most preferably between 20 and 40 $\mu$m.

In the embodiments of the invention according to principle A (in which drug-releasing areas are arranged over a skin-adhesion layer), it has proved advantageous for the adhesion layer to be applied to a support layer which is in contact with the drug reservoir. Arrangements without this support layer are, of course, possible, and may be advantageous with especially stable drug reservoir layers. The support layer has openings, preferably transit pores, which are partially or wholly filled up to the skin contact surface with drug-releasing material. Materials for forming this flexible support layer include, for example paper, plastic and metal sheets or textile sheets. The layer thickness should be between 5 $\mu$m and 2 mm, preferably between 10 $\mu$m and 500 $\mu$m.

If a secure union between the drug reservoir layer and the support layer cannot be provided by the self-adhesiveness of the reservoir, it can be achieved by applying an additional adhesive layer between the support material and the drug reservoir, whereby the adhesive forces within the entire system must be greater than those between the skin contact surface and the skin. The adhesive layer may cover the entire area of contact between the drug reservoir layer and the support layer, or it can also be confined to the areas of the support layer parallel to the skin. The adhesive to be used, as with the adhesives of the intermediate layer between the reservoir and the backing layer, must effect greater adhesion within the system than between the skin and the skin contact surface. The thickness of this adhesive layer varies preferably between 10 and 100 $\mu$m, especially between 20 and 40 $\mu$m.

In order to protect the skin contact surface and optionally also to avoid the escape of components of the drug reservoir from the open areas of the drug-releasing surface, the system according to the invention may be covered on the skin contact side by a protective layer which is detachable prior to application. It may be produced from the same materials as those used in the production of the backing layer, provided that they are of detachable construction, for example by applying a silicon layer. Other detachable protective layers which are generally known to persons skilled in the art are, for example, polytetrafluoroethylene, modified paper, cellophane, polyvinyl chloride etc. In order to render it readily detachable the protective layer may be provided in known manner with removing aids. The thickness of the protective layer is not critical, since it does not affect wearing comfort as it is removed before application. The thickness is suitably between 10 and 500 $\mu$m, preferably between 20 and 150 $\mu$m; however, it can also be very rigid—so as to avoid creases appearing in the system prior to application.

The process according to the invention for the production of the new therapeutic system involves a combination of steps known per se. In order to produce a therapeutic system according to the invention as in principle A (i.e. individual drug-releasing areas in an adhesive surface), adhesive base material is coated with skin-adhesion material and, in a second stage, the support layer is lined thereon. The laminate obtained in this way is then perforated by known methods, for example by punching or using a toothed or screen roller, whereby the geometrically required apertures can be determined by the choice of tool. In this perforation procedure, which optionally may be carried out at an elevated temperature, in each case the support layer and the adhesive layer are also perforated and the adhesive base is imprinted or even also perforated. The latter is removed in a further stage of the operation and is replaced by the detachable protective layer. Finally, the drug reservoir layer is applied in known manner onto the perforated skin-adhesion layer side of the laminate.

In the event that the drug reservoir layer is applied as a solution, the solvent must be evaporated off before further steps of the process are carried out. The consistency of the material applied as the drug reservoir is firstly adjusted so that it is certain to completely penetrate into the apertures of the laminate. The system is completed by lining a backing layer, which is optionally finished, with an adhesive layer (corresponding to the intermediate layer). The continuous strip obtained in this way can now be finished and packed as described above, taking into consideration the therapeutic requirements.

One preferred further embodiment of this process involves producing the drug reservoir layer on a backing layer which optionally has an adhesive finish, and is applied by lining under pressure or under pressure and heat to a laminate having apertures and consisting of the support layer and the skin adhesion layer.

If an additional adhesive layer is necessary for the union between the reservoir and support layer, this is applied to the support layer before perforation of the laminate comprising the support layer and skin adhesion layer. The laminate thus obtained can then be perforated directly or after being covered with a detachable auxiliary layer (e.g. silicon paper).

The auxiliary layer is removed again before applying or lining the reservoir layer.

When using support materials which already have suitable openings when manufactured, such as textile sheets (for example woven of fleecy material), the process should be modified in that the support material is coated in a first step with an adhesive on one side (for example by spraying) or on both sides (for example by immersing), and is placed on the detachable protective layer. The remaining steps of the process are as above following perforation, whereby the exchange of the adhesive base can be dispensed with.

Therapeutic systems according to principle A without the layer of support material can be made by preparing the drug-releasing areas in the desired arrangement, for example using a screen-printing process, on a protective layer, coating with an adhesive and covering with the backing layer.

Systems according to principle B, namely a drug-releasing area broken up by skin-adhesion sections, can be produced according to the invention by combining the steps of producing skin adhesion areas in a desired arrangement, using for example a screen printing process, on a repellent base material, which preferably serves as a protective layer; coating with drug-containing reservoir material; lining thereon the backing layer which optionally has an adhesive finish, and packaging. In this case also, the above-mentioned embodiment comprising the preparation of the reservoir layer on a backing layer which optionally has an adhesive finish can also be selected.

The preferred embodiments of the system according to the invention which are illustrated in FIGS. 5 and 6 can similarly be produced by the methods described; whereby the plasters as in FIG. 5, only the device bearing the skin adhesion material (for example screen printing stencil) must be designed accordingly, while with plasters as in FIG. 6, the perforation tool must be constructed accordingly. In both cases, the above relationship must be considered during finishing.

The invention will now be illustrated in more detail referring to the following Examples.

EXAMPLE 1

Therapeutic System According to Principle A

A layer of an acrylate copolymer solution (DUROTAK 280-2415, National Starch & Chemical B.V., Netherlands) (solids content: 44%, 93.3 parts acrylate copolymer + 6.7 parts colophony methyl ester in ethyl acetate) is applied to a paper-sheet with an adhesive finish attained by silconisation (weight per unit area: 95 g/m$^2$) by means of a roller. The thickness of the layer is such that an adhesive layer having a weight per unit area of 44 g/m$^2$ results after subsequent drying at 65° C. A polyamide non-woven fabric with a weight per unit area of 33 g/m$^2$ is then used to line the contact-adhesive face and the laminate is then brought to a heated screen roller of an embossing calender. The screen roller is designed with the following dimensions: staggered rows of truncated pyramids with a clearance of 2 mm; clearance of the frustums within a row: 2.5 mm; rhombic basal area of the frustums: 2.7 mm$^2$; rhombic crown area of the frustums: 0.48 mm$^2$; height of the frustums: 0.85 mm. Perforation is effected at 280° C. and yields a laminate in which the non-woven fabric and the adhesive layer have perforations in a regular arrangement with a total proportion of 9% of the total area. The silicon paper is removed and a siliconised polyester sheet (weight per unit area: 145 g/m$^2$) is added.

In order to produce the reservoir material, 32.5 parts of a copolymer based on methacrylic esters and dimethylamino-ethyl-methyacrylate (EUDRAGIT E, Röhm Pharma, Germany) are dissolved in 32.5 parts of methanol, and 30 parts of a mixture of toluene 2-octyl-dodecanol (1:1) are added. Then, 20 parts of the active substance, namely 4-(1-methyl-4-piperidylidene)-4H-benzo 4,5-cyclohepta-1,2-b thiophen-10 (9H)-one-hydrogen-fumarate (Ketotifen HFU), are added and dissolved. The viscosity of the mass is adjusted to 0.55 dPa.s with methyl ethyl ketone. The mass is applied to a non-adhesive side of the above-produced perforated non-woven laminate using a roller in such a layer thickness that, following drying at 65° C., a reservoir layer of 44 g/m$^2$ is obtained.

The backing layer with the adhesive finish is produced by coating a siliconised paper with an acrylate-copolymer solution (DUROTAK 280-2416, National Starch & Chemical B.V., Netherlands) in ethyl acetate (solids content: 41%) and lining the adhesive layer obtained after drying at 65° C., which has a weight of 30 g/m$^2$, onto an aluminised polyester film (weight per unit area: 20 g/m$^2$). The open side is then lined with the laminate comprising the reservoir layer, non-woven fabric and adhesive layer.

In the subsequent finishing process, plaster sections are punched out of the continuous strip obtained such that they correspond in size to therapeutical requirements. By punching the protective layer diagonally, an aid to removing the protective layer is created.

The product may be packed, for example, into suitable sealed bags.

EXAMPLE 2

Production of a Bopindolol-HMO Plaster

Production of the therapeutic system is analogous to Example 1, except for the production and composition of the drug reservoir material. This is produced in this case by dissolving 30.6 parts by weight of a methacrylic acid ester/dimethylaminoethylmethacrylate copolymer (EUDRAGIT E, Röhm Pharma, Germany), dissolved in 30.6 parts by weight of tetrahydrofuran, adding 25 parts by weight of (±)-1-(tert.-butylamino)-3-[(2-methyl-1-H-indol-4yl)-oxy]-2-propanol benzoate hydrogen malonate (Bopindolol HMO), 3.75 parts by weight of malonic acid and 10 parts by weight of 2-octyl-dodecanol, and adjusting the viscosity to 0.55 dPa.s with methyl ethyl ketone.

EXAMPLE 3

In vitro Release of Active Substances from the Therapeutic System

Punched forms of 16 m² of the laminates produced in Examples 1 and 2 are used as the therapeutic system and are reinforced on the backing layer with a plastic film which is adhesive on one side. The punched forms are placed in a container at 37° C. and exposed to an acceptor medium (80 ml of physiological sodium chloride solution), so that close contact with the walls of the container is avoided and the releasing side is always immersed. After 2, 4, 8 and 24 hours following the insertion of the punched form into the physiological sodium chloride solution, the acceptor medium is renewed. The amount of active substances released is determined by photometrical quantitative analysis. The ketotifen HFU concentration is evaluated by measuring the UV absorption at 265 nm and that of bopindolol HMU is evaluated by measuring the UV absorption at 265 nm.

Figure 7:
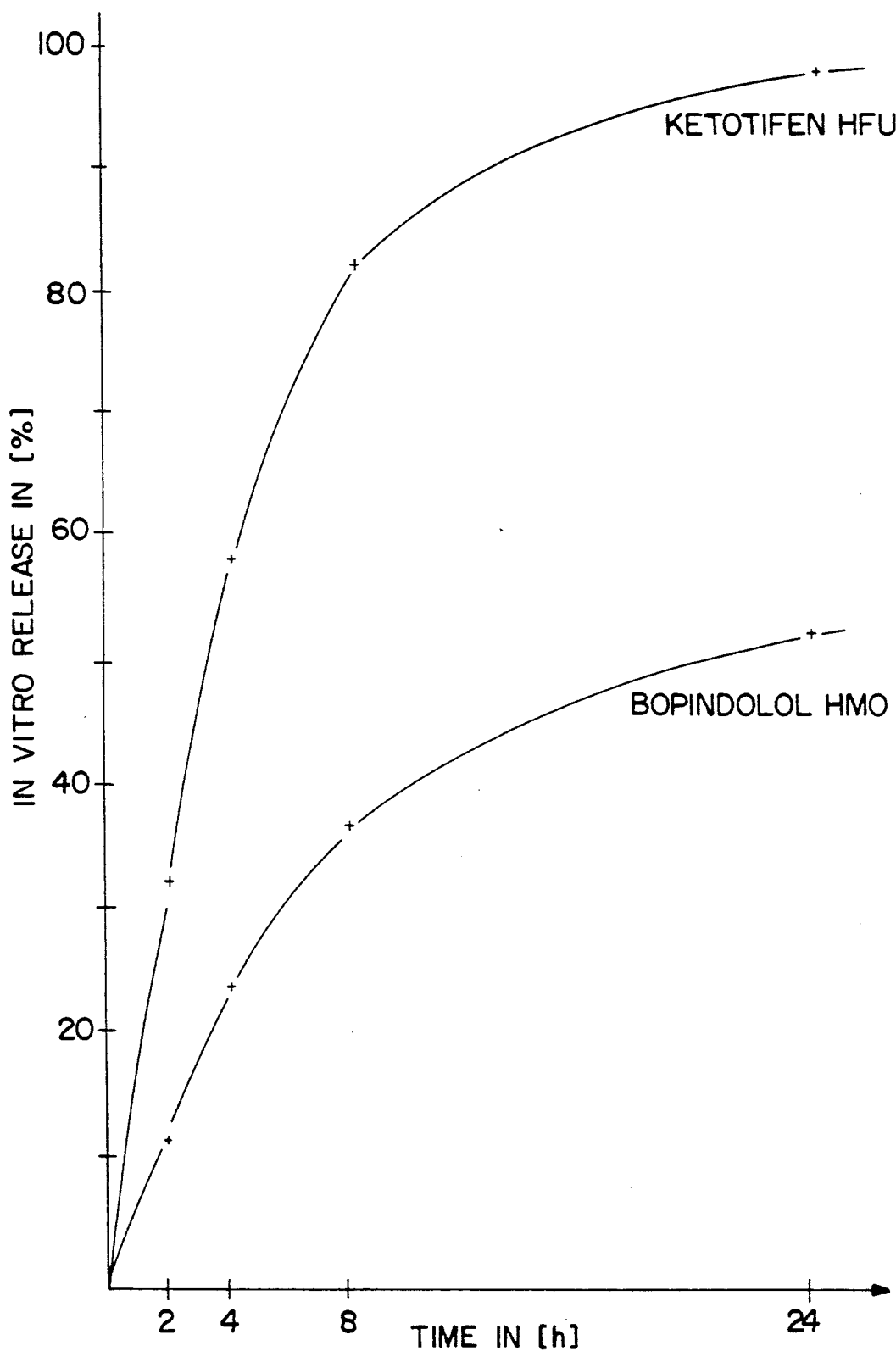
FIG. 7 illustrates graphically the rate of in vitro release of ketotifen and bopindolol from a therapeutical system according to an embodiment of the invention.

The results of this photometric examination are illustrated in FIG. 7, whereby the quantity of active substance released is shown as a percentage over time. This indicates that the releasing kinetics for both substances are the same, but as a result of the differing physical-chemical properties of ketotifen HFU and bopindolol HMO, quantitatively different amounts of substance are released dependent on time. However, both curves clearly show that there is a controlled release of active substance over 24 hours.

EXAMPLE 4

Ketotifen-Containing System According to Principle B of the Invention

A polyester film with a weight per unit area of 145 g/m², which has been siliconised to a different extent on each side, is coated in a screen printing process with an aqueous dispersion of a carboxyl-group containing acrylate copolymer (ACRONAL 80D, BASF, Ludwigshafen) (solids content: 55%), which has been set at a viscosity of 8 Pa.s by a thickener based on diurethane.

The screening drum has openings of 1.5 mm diameter, which are spaced at an average distance of 3.7 mm from one another, and result in an open area of the screening drum of 16.7%. Adhesive areas are arranged on the polyester film analogously to the screening drum and, after drying at 65° C., these have a weight per unit area of 30 g/m². The ketotifen-containing reservoir material described in Example 1 is applied by rollers as a further coat of the product. The process continues as in Example 1.

EXAMPLE 5

Production of a Bopindolol System According to Principle B of the Invention

A therapeutic system according to the invention is produced as described in Example 3, except that the drug reservoir material of Example 2 is applied.

EXAMPLE 6

Production of a Therapeutic System Having Different Active Substances in the Skin Adhesion Sections and Drug-Releasing Sections A drug-containing system as described in Example 4 is produced, except that lanata-$\beta$-acetyldigoxin in an acrylate system is used as the reservoir material, and nitroglycerine is used in the skin adhesion section.

We claim:

1. A multi-component planar therapeutic system for securement to skin and transdermal administration of drugs, said system comprising a planar skin contact area, said skin contact area comprising a drug-releasing component and an adhesive component presenting respective transdermal transfer and skin adhesion surfaces over said skin contact area in the same level said drug-releasing component forming part of a drug containing reservoir and wherein at least one of said drug-releasing component and said adhesive component is divided into discrete sections distributed over the entirety of said skin contact area to thereby ensure constant contact of said drug-releasing component with a region of skin for transdermal drug administration to the subject.

2. A planar therapeutic system according to claim 1, characterized by having discrete drug-releasing sections distributed over the skin contact area.

3. A planar therapeutic system according to claim 1, characterized by having drug-releasing sections which are circular in area.

4. A planar therapeutic system according to claim 1, characterized by having adhesive sections which are circular in area.

5. A planar therapeutic system accoding to claim 1, characterized by having adhesive sections and drug-releasing sections arranged in strips alternating side by side.

6. A planar therapeutic system according to claim 1 characterized in that said skin contact area is provided with a peripheral skin adhesion edge portion.

7. A planar therapeutic system according to claim 1, characterized in that it further includes a flexible backing layer facing away from the skin contact area of said system.

8. A planar therapeutic system acording to claim 7, characterized further by an adhesive intermediate layer disposed between the flexible backing layer and the drug-releasing component.

9. A planar therapeutic system according to claim 1, characterized by further including a supporting layer with openings in contact with the drug-releasing component.

10. A planar therapeutic system according to claim 9, characterized in that the supporting layer is formed of flexible material selected from the group consisting of paper, textile sheet, metal film, plastic film and laminates thereof.

11. A planar therapeutic system according to claim 9, characterized in that there is an adhesive component situated between the supporting layer and the drug-releasing component.

12. A planar therapeutic system according to claim 1, characterized in that the drug-releasing component contains at least one drug having topical action.

13. A planar therapeutic system according to claim 1, characterized in that the drug is comprised of the combination of a cardiac glycoside and a compound selected from the group consisting of vasodilators, musculotropic spasmolytics, coronary therapeutics and coronary vasodilators; an antihistamine and a compound selected from the group consisting of analeptics, analgesics, antipyretics, hypnotics, anaesthetics, antiseptics, musculotropic vasodilators, lipid lowering agents and vitamin B6; theophylline and compounds and derivatives thereof; and rubefacients and free bases, salts and derivatives thereof.

14. A planar therapeutic system according to claim 1, characterized in that the drug is selected from the group consisting of amphetaminil, betahistine, betaacetyl-digoxin, bopindolol, buprenorphine, clemastine, diclofenac, diltiazen, dimenhydrinate, diethylamine salicylate, ethyleneglycol, monosalicylate, 5-fluorouracil, glibenclamide, hydromorphone, ibuprofen, isopropyl-4-(2,1,3-benzoxydiazol-4-yl)-1,4-dihydro-5-methoxycarbonyl-2,6-dimethyl-3-pyridine-carboxylate, ketofin, L-thyroxine, nicotine, nicotinic acid-$\beta$-butoxyethylester, nonyl acid vanillylamide, pindolol, salbutamol, tamoxifin, tizanidine and theophylline.

15. A planar therapeutic system according to claim 1, characterized in that the drug of the drug-releasing component comprises a combination of a cardiac glycoside of digitales lanata-$\beta$-acetyldigoxin and a compound selected from the group consisting of vasodilators, musculotropic spasmolytics, coronary therapeutics and coronary vasodilators.

16. A planar therapeutic system according to claim 1, characterized in that the drug of the drug-releasing component comprises a combination of an antihistamine with a glucocorticoid.

17. A planar therapeutic system according to claim 1, characterized in that the drug of the drug-releasing component comprises a combination of a broncholytic, cardiac, diuretic, phospho-diesterase inhibitor, theophylline and compounds and derivatives thereof.

18. A planar therapeutic system according to claim 1, wherein the drug of the drug-releasing component comprises a rubefacient in combination with an antiphlogistic.

19. A planar therapeutic system according to claim 1, characterized in that at least one drug is present in the drug-releasing component and at least one other drug is present in the adhesive component.

20. A planar therapeutic system according to claim 1, characterized in that the adhesive component comprises nitroglycerine as an active agent thereof.

21. A process for the production of a planar therapeutic system as defined in claim 1, which comprises:
providing a base layer for application of adhesive thereon;
producing an adhesive component layer on the base layer;
layering a support material thereon;
perforating the laminate thus formed;
exchanging the base layer for a detachable protective layer;
coating the surface which is away from the protective layer with a drug containing reservoir mass;
lining a backing layer thereon; and packaging the system.

22. A process for the production of a planar therapeutic system according to claim 16, characterized in that after perforating the laminate, a coating of the drug-releasing component is made by lining with a drug-releasing component produced on the backing layer by the application of pressure.

23. A process for the production of a planar therapeutic system as defined in claim 1 which comprises:
applying discrete adhesive sections onto a protective base layer;
coating the adhesive sections and protective base layer with the drug containing reservoir;
lining a backing layer which optionally has an adhesive finish over the drug containing reservoir; and packaging the resulting system.

24. The process of using a planar therapeutic system according to claim 1 comprising applying the system for the local or systemic transdermal administration of drugs in human and veterinary medicine and in cosmetics.

25. A planar therapeutic system according to claim 1, characterized by having drug-releasing sections which are square in area.

26. A planar therapeutic system according to claim 1, characterized by having adhesive sections which are square in area.

27. A planar therapeutic system according to claim 7, further characterized by including a removable protective layer.

28. A planar therapeutic system according to claim 1, further characterized in that the drug-releasing component contains at least one drug having systemic action.

29. A planar therapeutic system according to claim 16, wherein the antihistamine is clemastin and the glucocorticoid is dexamethason.

30. A planar therapeutic system according to claim 1, wherein the drug comprises a combination of an antihistamine and a compound selected from the group consisting of vasodilators, analeptics, analgesics, hypnotics, musculotropic vasodilators, and vitamin B6.

31. A planar therapeutic system according to claim 30, wherein the antihistamine is antiemeticum-dimenhydrinate.

32. A planar therapeutic system according to claim 1, characterized in that the drug comprises a combination of a broncholytic, cardiac, diuretic, phospho-diesterase inhibitor and theophylline derivatives.

33. A planar therapeutic system according to claim 17, wherein the broncholytic, cardiac, diuretic, phospho-diesterase inhibitor is theophylline.

34. A planar therapeutic system according to claim 18, wherein the rubefacient is selected from the group consisting of nicotinic acid-$\beta$-butoxyethylester, nonyl acid vanillylamide and the antiphlogistic is selected from the group consisting of ethyleneglycol monosalicylate and diethylamine salicylate.

35. A process for the production of a planar therapeutic system according to claim 22, further characterized by applying heat along with the pressure to produce a coating of the drug containing reservoir mass.

36. A multi-component planar therapeutic system for securement to skin and transdermal administration of drugs, said system comprising a planar skin contact area, said skin contact area comprising a drug-releasing component and an adhesive component presenting respective transdermal transfer and skin adhesion surfaces over said skin contact area in the same level said drug-releasing component comprising a drug containing reservoir, and wherein at least one of said drug-releasing component and said adhesive component is divided into discrete sections distributed over the entirety of said skin contact area, each of said discrete sections being separated by surfaces of the other of said components, the surfaces of the discrete sections and separating surfaces all being at said same level thereby to ensure constant contact of said drug-releasing component with said region of skin for transdermal drug administration to the subject.

37. A planar therapeutic system according to claim 36 wherein said discrete sections are isolated from each other by regions of the other component.

* * * * *

UNITED STATES PATENT AND TRADEMARK OFFICE
CERTIFICATE OF CORRECTION

PATENT NO. : 5,132,115
DATED : July 21, 1992
INVENTOR(S) : K. Wolter et al

It is certified that error appears in the above-identified patent and that said Letters Patent is hereby corrected as shown below:

Claim 5

Column 12, Line 28, replace "accoding" with "--according--".

Signed and Sealed this

Twenty-sixth Day of October, 1993

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,132,115
DATED : July 21, 1992
INVENTOR(S) : K. Wolter et al

It is certified that error appears in the above-identified patent and that said Letters Patent is hereby corrected as shown below:

Column 2, line 21, delete "paster",
       line 52, after "drug-releasing", delete --in shape--, and
       line 52, after "sections", insert --in shape--.

Column 4, line 25, after "diethylamine", delete --,--, and
       line 64, delete "(Plane)", and insert therefor --(plane)--.

Column 6, line 61, delete "material", and
       line 61, after "matrix", insert --material--.

Claim 14

Column 13, line 8, after "ethyleneglycol", delete --,--.

Claim 17

Column 13, line 29 and 30, delete "theoph-ylline", and insert therefor --theo-phylline--.

Signed and Sealed this

Twenty-second Day of February, 1994

Attest:

BRUCE LEHMAN

Attesting Officer      Commissioner of Patents and Trademarks